United States Patent [19]

Koyama et al.

[11] Patent Number: 4,486,537

[45] Date of Patent: Dec. 4, 1984

[54] ANALYTICAL ELEMENT AND METHOD OF USE

[75] Inventors: Mikio Koyama; Kenichiro Okaniwa, both of Hino, Japan

[73] Assignee: Konishiroku Photo Industry Co., Ltd., Tokyo, Japan

[21] Appl. No.: 419,931

[22] Filed: Sep. 20, 1982

[30] Foreign Application Priority Data

Sep. 29, 1981 [JP]  Japan ............................... 56-155788

[51] Int. Cl.³ ...................... G01N 21/78; G01N 33/52
[52] U.S. Cl. .................................... 436/170; 422/56; 422/57; 435/805
[58] Field of Search .................................... 422/55–58; 435/805; 428/339, 407, 327, 442; 210/512; 436/170, 169

[56] References Cited

U.S. PATENT DOCUMENTS 3,992,158  11/1976  Przybylowicz et al. ............. 422/57
4,258,001   3/1981  Pierce et al. ..................... 436/170 X
4,356,149  10/1982  Kitajima et al. .................. 422/57 X Primary Examiner—Arnold Turk
Attorney, Agent, or Firm—Frishauf, Holtz, Goodman & Woodward

[57] ABSTRACT

An analytical element comprising a light-transmissive and liquid-impervious support, at least one reagent layer containing at least one reagent which reacts with a component in a fluid sample and at least one development layer provided at a position on the reagent layer on the opposite side to that of the support for permitting the component in said fluid sample to permeate into the reagent layer, at least one layer of reagent layers being constituted of polymeric particulate units each having a core-shell multi-layer structure comprising a core, which is hydrophobic and substantially unswellable with a fluid sample, and a hydrophilic outer shell.

16 Claims, No Drawings

ANALYTICAL ELEMENT AND METHOD OF USE

This invention relates generally to analytical chemistry, particularly to an analytical element for analysis of a predetermined specific component in a fluid. More particularly, it pertains to a quantitative analytical element for analysis of a specific component in a biological fluid sample.

There have been developed a large number of methods for analyzing the components of a liquid. These methods may be classified broadly into the reaction system using a liquid and the reaction system using a solid.

The analytical reaction in a solution system (hereinafter abbreviated as wet chemistry) includes a large number of procedures, varying widely from an analytical procedure of a so called manual method in which no machine is used at all to automatic quantitative analyzers frequently used in recent years in clinical diagnostic centers.

Among them, automatic quantitative analyzers are useful especially for the analysis of blood, and so on.

For example, the analyzer based on the continuous analysis as disclosed in U.S. Pat. No. 2,797,149 is typical of these automatic analyzers.

These analyzers will perform quantitative measurements by mixing a fluid sample, a diluent and an analytical reagent, transferring the mixture into an analytical device, where an analytical reaction and quantitative determination are conducted.

However, these continuous analyzers are complicated and expensive, requiring operational technique by an expert. Repeated washing operations are also necessarily required to be performed, for which enormous amounts of time and labor are consumed. In addition, waste liquors from such washings will inevitably cause the problem of environmental pollution.

On the other hand, there have been widely employed the analytical method in which the dry system reaction (hereinafter abbreviated as dry chemistry) is used.

For example, as disclosed in U.S. Pat. Nos. 3,050,373 or 3,061,523, a water-absorptive carrier such as filter paper is impregnated with a reagent solution and dried to prepare a test strip.

Generally, according to these methods, by adding dropwise a fluid sample on an analytical test paper or merely on a test strip, or by dipping a test strip in a fluid sample, and measuring the color change or density change of the test strip with the naked eye or by means of a reflection densitometer, the concentration level of a specific component in the fluid sample is determined.

These test strips are useful, since they are easy to handle and can give directly the result of a test, but its usefulness is still in the field of semi-quantitative analysis or qualitative analysis due to its constitution.

As contrasted to the analytical method of the prior art as described above, there is also proposed an analytical element to test blood as disclosed in Japanese Patent Publication No. 21677/1978, dry chemistry is used to achieve an easy, high-quantitative performance.

This is an analytical element to test blood, comprising at least one reagent layer which is positioned on one side of a light-transmissive and liquid-impervious support, and which contains at least one reagent reactive with the component in a fluid sample and is constituted of a hydrophilic colloid and at least one development layer of a non-fibrous porous medium layer which is positioned on the reagent layer on the opposite side to that of said support for permitting the component in said fluid sample to permeate into said reagent layer.

However, the above analytical element combined with a reagent layer of a hydrophilic colloid such as gelatin has the drawback that there are formed polymer matrixes of the hydrophilic colloid which are both permeable or impermeable to the component in a fluid sample.

That is, a water-soluble and low molecular weight compound such as glucose, urea in blood, uric acid, bilirubin, etc. can readily be diffused through the hydrophilic polymer matrix. On the other hand, a highly hydrophobic compound (e.g. lipids such as cholesterol ester, triglycerides, etc.) cannot be diffused through said matrix and therefore cannot react with the reagent existing in said analytical element. Thus, it has the serious defect of exhibiting no desired quantitative performance.

Further, a macromolecular protein or enzyme (e.g. glutamate: oxzaloacetate transaminase, glutamate: pyruvate transaminase, etc.) cannot likewise be diffused through the reagent layer and therefore analysis of such a substance is also impossible. Moreover, in Japanese Provisional Patent Publication No. 909859/1980, there is disclosed a porous particulate structure of an agglomerated three-dimensional lattice comprising non-swellable, liquid-impervious and heat-stable organic polymer particles adhered to each other with an adhesive of a polymer different from said polymer particles.

According to the above patent, an adhesive polymer which is low in thermal stability, namely low in glass transition temperature (Tg) is thermally softened at a temperature or Tg of higher to effect adhesions between the thermally stable organic polymers, thereby forming a particulate structure having mutually interconnected spaces. Accordingly, when a large amount of an adhesive is used for formation of the particulate structure disclosed in the above patent, the void volume will be reduced. On the other hand, at too low a level of an adhesive, no sufficient adhesion strength can be attained. Thus, it is required to use a specified amount of the above adhesive and also to arrange all of the adhesive at desirable positions between the above thermally stable polymer particles, and consequently it is difficult to control the void volume at a certain value. Another drawback is low adhesion strength, because inert beads are bound only through deformation by thermal softening of an adhesive.

The above patent also suffers from the drawback in its functional aspect in that development of a fluid sample is carried out in the lateral direction, whereby the fluid sample developed in the lateral direction in the development layer in application onto the reagent layer may further be developed in the lateral direction in the reagent layer, namely to cause so called secondary development, resulting in lowering of detection sensitivity. Moreover, since the element is constituted of a hydrophobic polymer, it is very difficult to hold a fluid sample therein and therefore no sufficient analytical reaction can be completed within said layer.

The present inventors have made extensive studies and were successful to overcome the above drawbacks by use of an analytical element having the constitution as specified below.

That is, the analytical element of the present invention comprises a light-transmissive and liquid-impervious support, at least one reagent layer containing at least one reagent which reacts with a component in a fluid sample and at least one development layer provided at a position on the reagent layer on the opposite side to that of said support for permitting the component in said fluid sample to permeate into said reagent layer, at least one layer of reagent layers being constituted of polymeric particulate units each having a core-shell multi-layer structure comprising a core, which is hydrophobic and substantially unswellable with a fluid sample, and a hydrophilic outer shell.

The analytical element of the present invention can rapidly receive a fluid sample within the reagent layer thereof, irrespective of whether the molecular weight of the substance to be analyzed contained in said fluid sample may be low or high, or whether it may be water soluble or hydrophobic.

That is, the analytical element of the present invention has a constitution which can readily receive an applied fluid sample containing various analytes, and also enable uniform distribution of the sample within the analytical element. At least one of the reagent layers of the present invention is constituted of polymeric particulate units each having a core-shell double layer structure comprising a core, which is preferably hydrophobic and substantially unswellable with a fluid sample, and a hydrophilic shell surrounding said core, said units being bound at the contacted portions of said units through mutual adhesion between the hydrophilic outer shell portions.

These polymeric particulate units have a specified amount of voids and evidently have sufficient strength to maintain their appearance and structure against physical external forces.

On the other hand, the voids in the above structure will of course permit substantially no development in the lateral direction when in contact with a fluid sample.

The above polymeric particulate units may have sizes preferably in the range from about 0.1 to about 200 microns, more preferably from about 0.3 to 100 microns.

The reagent layer constituted of these particulate units can also have any desired void volume within the range from about 20 to about 85%.

Further, the ratio of the hydrophilic portion to the hydrophobic portion constituting the particulate units of the present invention can be selected as desired, so long as the voids in said reagent layer are not clogged by the fluid sample applied.

That is, the hydrophilic portion is about 90 to about 0.05% by weight, while the hydrophobic portion is about 99.95 to about 10% by weight. Preferably, the hydrophilic portion is about 50 to about 0.1% by weight, while the hydrophobic portion about 99.9 to about 50% by weight. More preferably, the hydrophilic portion is about 25 to about 0.5% by weight, while the hydrophobic portion is about 99.5 to 75% by weight.

The core portion of the polymeric particulate unit is hydrophobic and does not substantially swell when in contact with a fluid sample.

The degree of swelling can be measured by, for example, a swellometer of the type as shown in A. Green & G. I. P. Levenson, Journal of Photographic Science, Vol. 20, pp. 205 (1972), under a desired fluid.

That is, on a polyethylene terephthalate support, there is formed (1) a self-supporting film of the high molecular polymer under consideration to be used as the particulate material, or (2) a layer with a dried film thickness of 50 to 100 microns, then the percent increase of said film or layer when dipped in a liquid bath at 38° C. for about 25 minutes is measured by means of the aforesaid swellometer. A material having a swelling degree of less than about 20%, preferably less than about 10%, as measured by these methods, may preferably be used as the high molecular polymeric particulate unit material.

As the monomers constituting the core of the present invention, being hydrophobic and non-swellable with a fluid sample, there may be employed any desired monomer so long as it can satisfy the conditions as of such monomers.

For example, there may be included styrenes, such as styrene, p-chlorostyrene, etc.; acrylates such as methyl acrylate, ethyl acrylate, n-butyl acrylate, etc.; methacrylates, such as methyl methacrylate, ethyl methacrylate, n-butyl methacrylate, etc.; (meth)acrylonitriles such as acrylonitrile, methacrylonitrile, etc.; vinyl halides such as vinyl chloride, vinyl fluoride, etc.; vinylidene halides such as vinylidene chloride, vinylidene fluoride, etc.; conjugated dienes such as 1,3-butadiene, isoprene, 2,3-dimethyl-1,3-butadiene, etc.; crosslinking monomers such as divinyl benzene, ethyleneglycol dimethacrylate, etc.; and further monomers having non-radical poymerizable functional groups such as glycidyl methacrylate, aziridylethyl methacrylate, vinyl isocyanate, etc.

On the other hand, the hydrophilic polymer portion forming the outer shell of the polymeric particulate units of the present invention can also employ various water-soluble polymers and water-soluble monomers capable of forming water-soluble polymers as desired.

For example, as water-soluble polymers, there may be employed gelatins such as gelatin, acid-treated gelatins; water-soluble cellulose derivatives such as carboxymethyl cellulose, hydroxyethyl cellulose, etc.; pullulane or pullulane derivatives such as carboxymethyl pullulane; and water-soluble vinyl polymers such as polyvinyl alcohol, polyvinyl pyrrolidone, polyacrylamide, polymethacrylamide, etc.

Further, the aforesaid water-soluble monomers may be used by polymerizing in various ways. For example, there may be mentioned vinyl acid amides such as acrylamide, methacrylamide, etc.; vinyl heterocyclic compounds such as N-vinylpyrrolidone, N-vinylimidazole, etc.

As described above, it is possible to form the polymeric particulate units of the present invention by using various hydrophobic monomers and water-soluble polymers or monomers capable of forming water-soluble polymers in combination.

These polymers may be synthesized according to any desired method, which is not particularly limited. Generally, however, they can readily be synthesized by combination of known techniques such as emulsion polymerization, suspension polymerization, seed polymerization, microencapsulation, etc.

In the following, there are shown examples of the polymeric particulate units according to the present invention, by which the present invention is not limited.

Exemplary polymeric particulate units:
(1) Polyvinyl alcohol/styrene (polymerization ratio: 5/95);
(2) Polyvinylpyrrolidone/(styrene:methyl methacrylate =50:50 weight ratio) (weight ratio: 8/92);
(3) Gelatin/styrene (weight ratio: 2/98);

(4) Hydroxyethyl cellulose/methyl methacrylate (weight ratio: 12/88);

(5) Gelatin/(styrene:divinylbenzene=98:2 weight ratio) (weight ratio: 7/93);

(6) Methyl cellulose/(butadiene:acrylonitrile=50:50 weight ratio) (weight ratio: 1/99);

(7) Polvinylpyrrolidone/ethyl acrylate (weight ratio: 15/85);

(8) Gelatin/polystyrene (weight ratio 5/95);

(9) Gelatin/copoly(styrene:glycidyl methacrylate=95:5 weight ratio) (weight ratio: 2/98);

(10) Polyvinyl alcohol/polymethylmethacrylate (weight ratio: 30/70);

(11) Polyvinyl alcohol/polyethylacrylate (weight ratio: 20/80)

(12) Polyacrylamide/copoly(styrene:divinylbenzene=98:2 weight ratio) (weight ratio: 3/97);

(13) polyvinyl alcohol/copoly(styrene:n-butyl methacrylate=70:30 weight ratio) (weight ratio: 15/85).

(14) Methyl cellulose/polyacrylic acid (weight ratio: 20/80);

(15) Copoly(vinylpyrrolidone/styrene/methyl methacrylate) (weight ratio: 5/80/15);

(16) Copoly(acrylamide/N-vinylpyrrolidone/styrene) (weight ratio: 5/3/92);

(17) Copoly(isopropylacrylamide/hydroxyethyl methacrylate/methyl methacrylate) (weight ratio: 10/2/88);

(18) Copoly(methacrylamide/N-vinylpyrrolidone/styrene) (weight ratio: 15/5/80);

(19) Copoly(N-vinylimidazole/N-vinylpyrrolidone/styrene) (weight ratio: 15/3/82).

The following synthesis examples for preparation of the polymeric particulate units are presented for illustration of the present invention, by which the present invention is not limited at all.

SYNTHESIS EXAMPLE 1

Synthesis of exemplary polymeric particulate units (1)

A mixture of a monomer and a polymerization initiator, comprising 160 g of styrene and 4.8 g of 2,2'-azobis(2,4-dimethylvaleronitrile) was added into 700 ml of a solution containing 3% by weight of trisodium phosphate and 5% by weight of a polyvinyl alcohol (completely saponified product produced by Nippon Gosei Kagaku Co.) based on the above monomer under stirring by means of TK-homojetter (produced by Tokushu Kika Kogyo Co.) at 8000 r.p.m. After the addition, stirring was continued for 30 minutes, and on reaching a particle size of about 8 micron as observed by microscope, the mixture was placed into a four-necked flask equipped with a stirring means, a cooling tube, a nitrogen gas inlet tube and a thermometer. Polymerization was then carried out under nitrogen stream with stirring at 200 r.p.m. at 60° C. for 24 hours to complete polymerization. Then, the contents were cooled to room temperature, trisodium phosphate was removed by decomposition with a dilute aqueous hydrochloric acid solution. After repeated washing with water, the polymer particles were filtered and dried to give polymeric particulate units with an average particle size of about 7 microns.

SYNTHESIS EXAMPLE 2

Synthesis of exemplary polymeric particulate units (9)

While stirring a solution containing 8 g of an alumina (AEROSIR Aluminum Oxide C (trade name) produced by Nippon Aerosil Co.) and 0.064 g of sodium dodecylbenzenesulfonate in 500 ml of degassed distilled water by means of TK-homojetter at a speed of 10000 r.p.m., a mixture of monomers and a polymerization initiator comprising 76 g of styrene, 4 g of glycidyl methacrylate and 2.4 g of 2,2'-azobis(2,4-dimethylvaleronitrile) was added thereto, and the oil droplets were adjusted to have particle sizes of about 2 microns. After stirring for additional 30 minutes, the mixture was placed in a pressure bottle and polymerization was carried out in an oven at 60° C. for 24 hours. Then, taking out from the oven and being cooled to room temperature, the polymer was collected by filtration, further dispersed again in an alkaline aqueous solution of about pH 10, followed by sonication by an ultrasonic homogenizer under stirring to remove the alumina on the polymer surface. The above polymer was filtered off, washed repeatedly with water and dried. After 50 g of the dried polymer was dispersed again in 500 ml of an aqueous solution containing 2.5 g of deionized gelatin, 750 ml of ethyl alcohol was gradually added under stirring to effect encapsulation of the deionized gelatin on the surface of polymer particles. Further, with continued stirring, hydrochloric acid was added to adjust the pH to about 1.0, and the temperature was elevated to 50° C., whereat the reaction was carried out for 30 minutes. The above polymer dispersion was filtered and washed with water until the filtrate became neutral, followed by drying, to give polymeric particulate units with an average particle size of about 2 microns.

SYNTHESIS EXAMPLE-3

Synthesis of exemplary polymeric particulate units (16)

In a four-necked flask equipped with a stirring means, a cooling tube, a nitrogen inlet tube and a thermometer, 4.0 g of a polyoxyethylene nonylphenylether (n=30) and 0.01 g of sodium dodecylbenzenesulfonate were dissolved in 500 ml of degassed distilled water, and 2.1 g of N-vinylpyrrolidone and 97.9 g of styrene were added to the solution. The mixture was stirred under nitrogen stream at a stirring speed of 200 r.p.m., and the temperature in the flask was elevated gradually to 60° C. Then, aqueous solutions having dissolved 0.25 g of sodium persulfate and 0.15 g of sodium sulfite, respectively, in 20 ml of degassed distilled water were added at the same time, and the reaction was carried out at a stirring speed of 200 r.p.m. at 60° C. for 10 hours, followed by filtration, to obtain a latex solution.

The above latex solution was further charged into a four-necked flask equipped with a stirring means, a cooling tube, a nitrogen inlet tube and a thermometer, and 5 g of acrylamide was added and dissolved by stirring at room temperature under nitrogen stream at a stirring speed of 250 r.p.m. The above contents were elevated to 50° C. and adjusted to around pH 1.5 with conc. nitric acid. Further, an aqueous solution having 1.1 g of $Ce(NH_4)_2(NO_3)_6$ dissolved in degassed distilled water was added dropwise slowly over one hour. After completion of the dropwise addition, the reaction was continued at the same temperature and the same stirring speed for 8 hours to complete the reaction. The contents were cooled to room temperature, filtered and placed in a cellophane dialysis tube. After dialysis in pure water for one week, the product was obtained after concentration. The product was found to have an average particle diameter of about 0.9 micron.

The reagent layer using the polymeric particulate units in the present invention is bound and can maintain its structure through fusion between the hydrophilic polymer portions forming the outer shells of said particles.

The diameter of the voids formed thereby depends on the particle sizes of the particulate units employed.

That is, it is believed that voids with pore diameters of about ½ to about 1/10 as much as the size of said particles are formed.

By this correlation, any desired pore diameter can be obtained.

The pore diameter should be selected depending on the size of the object to be analyzed. For example, in case of a low molecular compound such as glucose, uric acid and other substrates, said particulates units may have a size of about 0.05 micron.

In case of a hydrophobic low molecular compound cholesterol ester, it is possible to use particulate units with a size of about 0.1 micron or more.

Further, in case of an enzyme which is a protein, the particulate units are desired to have a size of about 1 micron or more.

Further, the voids constituted of said particulate units should of course be within the range which will not substantially permit a fluid to develop in the lateral direction.

The reagent layer of the present invention can contain reagents necessary for analysis of the substance to be analyzed.

These can contain, if said substance to be analyzed is a substrate, an enzyme to decompose said substance into a detectable compound, or if it is an enzyme, a substrate specific for the enzyme.

It is also possible to incorporate in the reagent layer a compound to change variously the above detectable compound.

Further, an additive substance in carrying out the analytical reaction such as a buffer or a preservative may also be added.

Of course, these reagents may be added all in one reagent layer, or alternatively separately in a plural number of reagent layers.

It is also possible to use a reagent layer comprising a hydrophilic colloidal substance in combination. For example, it is also possible to combine the reagent layer of the present invention with a reagent layer comprising a hydrophilic colloidal substance, incorporate macromolecules in the reagent layer of the present invention to permit the analytical reaction to proceed therein, and allow the compound formed diffusing into the matrix of the hydrophilic colloid to be diffused into the reagent layer of the lower layer comprising a hydrophilic colloid thereby to convert it to a detectable substance.

A dispersion useful for preparation of the reagent layer of the present invention is required to be stable for a time sufficient to apply said dispersion on a support.

For preparation of such a stable dispersion, it is possible to use various methods singly or in combination. For example, one useful method comprises adding a surfactant and a polymer into a liquid carrier as an accelerator or a binder useful for distribution or stabilization in the fiber dispersion.

As useful surfactants, there may be employed all surfactants of either ionic(anionic or cationic) or nonionic, but preferably nonionic surfactants are more effective. Examples of nonionic surfactants are polyalkyleneglycol derivatives of alkyl-substituted phenols such as 2,5-di-t-butylphenoxy polyethyleneglycol, p-octylphenoxy polyglycidylether, p-iso-nonylphenoxy polyethylene glycol, and polyalkyleneglycol esters of higher fatty acids. These surfactants have the effect of controlling the permeation speed of a liquid sample into the development layer of a fibrous structure simultaneously with the effect of inhibiting generation of undesirable "chromatography phenomenon". Further, as the effect of a surfactant, there is also the effect of alleviating various undesirable influences by proteins contained in a biological fluid sample.

The above surfactant may be employed in an amount which can be widely varied, but generally in an amount of 10 to 0.005% by weight based on the weight of the fibers, preferably 6 to 0.05% by weight. Further, as an alternative method, there may be employed sonication treatment, physical mixing, and physical stirring treatment and pH adjustment of said particles and liquid carrier.

These methods can be more effective by combination with the aforesaid method.

The aforesaid liquid carrier emloyed may be an aqueous liquid.

However, there may also be employed other liquid carriers such as various organic liquids provided that said particles are insoluble in such carriers and therefore the characteristics of the particles can be maintained.

Typical liquid carriers other than water may include organic solvents miscible with water, aqueous solutions of water with organic solvents miscible with water and suitable organic solvents immiscible with water.

Organic solvents miscible with water may be exemplified by lower alcohols (namely, alcohols with alkyl moieties having 1 to 4 carbon atoms), acetone and tetrahydrofuran.

Organic solvents immiscible with water may be inclusive of lower alkyl esters such as ethyl acetate and halogenated organic solvents such as halogenated hydrocarbons (e.g. chloroform, methyl chloride and carbon tetrachloride).

Further, the reagents to be incorporated in the reagent layer of the present invention may be incorporated according to conventional methods. For example, a water soluble reagent may be added as a solution, or a water insoluble reagent may be incorporated by the method generally known by the name of the oil protect dispersion method and the direct dispersion method conventionally used in the field of photography.

The reagent layer of the present invention, including other layers, may be applied by various coating methods such as the dip coating method, the air knife method, the curtain coating method or the extrusion coating method using a hopper as disclosed in U.S. Pat. No. 2,681,294. If desired, two or more layers may be coated simultaneously according to the method as disclosed in U.S. Pat. No. 2,761,791 and U.K. Pat. No. 837,095.

Further, the drying temperature may be preferably set at a temperature such that the hydrophilic polymer portions of the outer shells of the particulate units of the present invention can be fused, and that the reagent contained, especially proteins such as enzyme, may not be denatured. For example, there may be employed a temperature of about 55° C. or lower, preferably about 50° C. or lower.

The aforesaid liquid-impervious, light-transmissive support according to the analytical element of the present invention (hereinafter abbreviated as the support according to the present invention) may be any kind of support, so long as it is impervious to liquids and light-transmissive. For example, various polymeric materials such as cellulose acetate, polyethylene terephthalate, polycarbonate or polystyrene are suitable for the purpose of use. In this case, the above support may have a thickness which can freely be selected, but preferably in the range from about 50 microns to 250 microns. The one side surface on the observation side of the support according to the present invention may also be freely worked depending on the purpose intended. Further, a light transmissive undercoating layer may also be used in some cases on the side of the support where a reagent layer is to be laminated to improve the adhesion between the reagent layer and the support.

The development layer of the present invention may be selected from any of layers, so long as it is provided with the performances as described in Japanese Patent Publication No. 21677/1978, namely:

(1) To distribute a constant volume of a fluid sample uniformly to a constant volume per unit area through the reagent layer;
(2) To remove substances or factors which interfere with the analytical reactions in the fluid sample;
(3) To effect a background action which reflects the measured light transmitted through the support during spectrophotometric analysis.

Accordingly, the development layer according to the present invention can perform all the three functions as mentioned above, but the three functions may also suitably be separated by use of the layers having respective functions. Further, it is also possible to use a layer having two of the three functions and a layer having the other remaining function. For example, there may be mentioned a development layer of a non-fibrous porous medium called as the brush polymer comprising titanium dioxide and cellulose diacetate as disclosed in the above Patent, and the development layers of fibrous structure as disclosed in Japanese Provisional Patent Publication No. 24576/1981, Japanese Patent Application No. 13203/1981 and Japanese Patent Application No. 65446/1981. In particular, the above development layer of fibrous structure is particularly useful as a material enabling rapid delivery of blood cells, and further useful for development delivery of macromolecules which is one of the objects of the present invention.

The analytical element of the present invention can take any desired arrangement among various different arrangements. Further, it is also possible to constitute the analytical element in conformity with the object of the present invention by combining the reagent layer of the present invention optionally with various functional layers, reagent containing layers and members, as exemplified by the reagent layer, reflection layer, undercoating layer as disclosed in U.S. Pat. No. 3,992,158, radiation blocking layer as disclosed in U.S. Pat. No. 4,042,335, barrier layer as disclosed in U.S. Pat. No. 4,066,403, registration layer as disclosed in U.S. Pat. No. 4,144,306, migration inhibition layer as disclosed in U.S. Pat. No. 4,166,093 scintillation layer as disclosed in U.S. Pat. No. 4,127,499, scavenging layer as disclosed in Japanese Provisional Patent Publication No. 90859/1980 and destructive pod-like member as disclosed in U.S. Pat. No. 4,110,079, and the like.

The methods of preparation of the aforesaid layers and the methods for incorporation of the aforesaid layers in the analytical element of the present invention may be the same as or similar to those as disclosed in said patents. In the aforesaid patents, there are also disclosed useful materials available in preparation of such layers.

Various layers in the analytical element are brought into fluid contact with each other. In the present specification, the expression "fluid contact" refers to the layers co-operating with each other in a mode so that a fluid (liquid or gaseous) can be passed from one layer to the other layer under the conditions employed. Such a fluid contact performance may preferably be uniform along the contact interface between the fluid contact layers. The fluid contact layers may be positioned adjacent to each other, or alternatively apart from each other through an intervening zone.

Such an intervening zone, however, is also under fluid contact and therefore will not impede passage of a fluid.

The reagent layer of the present invention may conveniently contain one or more reagent compositions. On interaction with an analyte, or a reaction product or decomposed product of an analyte, or on application of a fluid sample containing an analyte to an analytical element having incorporated the reagent layer, one or more of mutually interactive components are contained in the aforesaid composition. By such an interaction, release of detectable species previously formed within the element, formation of detectable species or formation of detectable changes within the element can be rendered possible.

The expression "interaction" means chemical activity, catalytic activity (formation of enzyme-substrate conjugate formation), immunogenic activity (antigen-antibody reaction) and any other form of electrical, chemical or physical action.

Through these electrical, chemical or physical actions, it is possible to release, form or provide detectable changes within the element. By the aforesaid changes, there can be exhibited directly or indirectly the presence and/or concentration of the analyte or the reaction product or decomposed product thereof.

The detectable change formed may preferable be detected by radiation measurement. The radiation measurement refers to a detection by use of an electromagnetic radiation measurement such as colorimetric measurement, fluorescence measurement, radiation counting, phosphorescence measurement and emission measurement.

As various detectable components to be used in the present invention, there may self-evidently be included dyes, pigments and complexes detectable by colorimetric measurement; dyes, pigments and complexes detectable by fluorescence measurement; emission tags; radioactive tags; chemical reagents; antigens; haptens; immunological medicines such as antibodies and antibody-antigen conjugates; enzymes; and precursors and reaction products of said components.

Uses of these components are disclosed in detail in U.S. Pat. No. 3,992,158, Belgian Pat. No. 862,955 and European Provisional Patent Publication No. 0002963.

In case of the analytical element of the present invention, any of whole blood, serum and plasma may conveniently be used. Further, it is also possible to use suitably other body fluids such as urine, lymph, neurolymph, etc.

When whole blood is used, there may be provided, if necessary, the radiation blocking layer or other reflection layer in order to avoid obstruction of the radiation for detection by the blood cells. When the color of the blood cells is to be observed directly, for example, in case of hemoglobin analysis, it is not of course necessary to provide the above reflection layer.

After analysis results are obtained as detectable changes by use of the analytical element of the present invention, corresponding to the various detectable changes, measurements are performed according to reflection spectrophotometry, emission spectrophotometry or reflection fluorescence spectrophotometry, or scintillation measurement. The thus obtained measured values can determine the amounts of unknown substances to be tested with reference to the calibration curve previously prepared.

The analytical element of the present invention having the constitution as described above can accomplish its object by supplying a fluid sample from the side of the development layer and then observing the analytical reaction from the side of the transparent support.

A fluid sample to be applied to the analytical element according to the present invention may be used in an amount as desired, but preferably in an amount of about 50 µl to about 5 µl, more preferably about 20 µl to about 5 µl. Usually, it is preferred to use about 20 µl of a fluid sample.

The analytical reaction to be employed for the analytical element of the present invention may be determined suitably depending on the purpose of analysis. For example, it may be used for fields of clinical chemistry, particularly be used for analysis of biological fluid samples such as blood or components in urine.

These can be constituted easily by suitable selection of analytical reagents so as to be available for analysis of a number of components, including low molecular compounds such as glucose, urea nitrogen, ammonia, uric acid, cholesterol, triglyceride, creatine, creatinine, bilirubin, etc. and protein enzymes such as glutamate-oxaloacetate transaminase, glutamate-pyruvate transaminase, lactic acid dehydrogenase, etc.

The present invention is described in further detail by referring to the following Examples, by which the embodiments of the present invention are not limited at all.

EXAMPLE-1

On a transparent polyethyleneterephthalate support with a thickness of about 180 microns, on which subcoating had already been applied, there were provided a reagent layer-I of the present invention and a reagent layer-I of Control with compositions indicated in Table I, respectively, then development layer with the composition indicated in Table II on the reagent layer of the present invention and the reagent layer of Control, respectively, to provide the analytical elements of the present invention-I, II and Control analytical elements-I, II as shown in Table III.

TABLE I

| No. | Reagent layer composition |
| --- | --- |
| Reagent layer - I of the present invention | Reagent layer of about 20 µ-dried film thickness comprising 0.35 g/dm$^2$ of exemplary polymeric particulate units (1) of the present invention with average particle size of about 7µ and 0.015 g/dm$^2$ of activator* |
| Control reagent layer - I | Reagent layer of about 20 µ-dried film thickness comprising 0.22 g/dm$^2$ of gelatin and 0.015 g/dm$^2$ of activator* |

*p-nonylphenoxypolyethyleneoxide

TABLE II

| No. | Development layer composition |
| --- | --- |
| Development layer - I | Development layer with about 300 µ-dried film thickness as disclosed in Japanese Patent Application No. 65446/1981, comprising 0.75 g poly(styrene-co-glycidyl methacrylate) weight ratio 90/10), 14 ml of xylene, 5 g of fiber and 0.5 g of octylphenoxypolyethoxyethanol |
| Development layer - II | Development layer with about 150 µ-dried film thickness as disclosd in U.S. Pat. No. 3,992,158, comprising 0.3 g/dm$^2$ of titanium dioxide and 0.037 g/dm$^2$ of cellulose diacetate |

TABLE III

| Sample No. | Reagent layer | Development layer |
| --- | --- | --- |
| Sample - I | Reagent layer - I of the present invention | Development layer - I |
| Sample - II | Reagent layer - I of the present invention | Development layer - II |
| Control sample - I | Reagent layer - I of Control | Development layer - I |
| Control sample - II | Reagent layer - I of Control | Development layer - II |

On the Samples and Control samples as prepared above, 10 microliter of a 5% aqueous bovine serum albumin solution (hereinafter referred to as BSA) was added dropwise. After drying, the above-mentioned development layer was removed, and each reagent layer was tested by way of coloration reaction according to the microbiuret method to confirm the presence of BSA.

As the result, no coloration based on BSA was exhibited on the reagent layers of Control sample-I and Control sample-II, thus showing markedly inferior holding capacity. On the other hand, the reagent layers of Samples-I and -II of the present invention exhibited clear colorations, thus indicating that the reagent layers of the present invention are excellent in the function of holding sufficiently the components in a fluid.

EXAMPLE-2

The exemplary polymeric particulate units-(1) in the reagent layer-I of the present invention in Example 1 was changed to the exemplary polymeric particulate units-(9) with an average particle size of about 2 microns, and further to the compositions of the reagent layers of the present invention and Control, there were added 0.75 g/m$^2$ of 4-methoxy-1-naphthol, 600 units/m$^2$ of cholesteroloxidase, 2000 units/m$^2$ of cholesterol-esterase, 0.215 g/m$^2$ of dimedone and 7000 units/m$^2$ of peroxidase. Otherwise, under the same conditions as in preparation of Samples-I, II and Control samples-I, II in Example 1, there were prepared Samples-III, IV and Control samples-III, IV.

On these samples, 10 microliter each of 100 mg/dl, 200 mg/dl standard aqueous cholesterol solutions and standard serum was added dropwise. After incubation at 36° C. for 10 minutes, the reflection density was measured with red light by means of Sakura Densitometer PDA-65 (produced by Konishiroku Photoindustry Co.).

TABLE IV

| Sample No. | Reflection density ($D_R$) | | | Standard serum |
|---|---|---|---|---|
| | Fogging | Cholesterol standard soln. | | |
| | | 100 mg/dl | 200 mg/dl | |
| Sample - III of the present invention | 0.15 | 0.38 | 0.58 | 0.41 |
| Sample - IV of the present invention | 0.22 | 0.36 | 0.53 | 0.48 |
| Control sample - III | 0.20 | 0.21 | 0.21 | 0.20 |
| Control sample - IV | 0.23 | 0.22 | 0.23 | 0.21 |

As the result, as shown in Table-IV, substantially no coloration occurred in Control samples, indicating that no cholesterol or cholesterol ester is held in the reagent layer. In contrast, all the samples according to the present invention exhibited good coloration, thus indicating that the reagent layer of the present invention can sufficiently fulfil its desired function.

We claim:

1. An analytical element, comprising a light-transmissive and liquid-impervious support, at least one reagent layer containing at least one reagent which reacts with a component in a fluid sample and at least one development layer provided at a position on said at least one reagent layer on the opposite side to that of said support for permitting the component in said fluid sample to permeate into said at least one reagent layer, wherein at least one reagent layer of said at least one reagent layers is composed of polymeric particulate units each having a core-shell multilayer structure comprising a hydrophobic core, which is substantially non-swellable when in contact with a fluid sample, and a hydrophilic outer shell, wherein the polymeric particulate units are bound to adjacent polymeric particulate units by mutual adhesion of the respective hydrophilic outer shells, said polymeric particulate units forming voids which substantially impede the development of a fluid sample in the lateral direction.

2. The analytical element of claim 1, wherein said polymeric particulate units consist of about 90 to about 0.05% by weight of the hydrophilic outer shell and about 99.95 to about 10% by weight of the hydrophobic core.

3. The analytical element of claim 1, wherein said polymeric particulate units consist of about 25 to about 0.5% by weight of the hydrophilic outer shell and about 99.5 to about 75% by weight of the hydrophobic core.

4. The analytical element of claim 1, wherein said hydrophobic core has a degree of swelling of less than about 20%.

5. The analytical element of claim 1, wherein said core consists of a polymer of at least one monomer selected from the group consisting of styrenes, acrylates, methacrylates, acrylonitriles, methacrylonitriles, vinyl halides, vinylene halides, conjugated dienes, crosslinking monomers, and monomers having non-radical polymerizable functional groups.

6. The analytical element of claim 1, wherein said outer shell consists of at least one water-soluble polymer selected from the group consisting of gelatins, water-soluble celluloses, pullulanes, and water-soluble vinyl polymers, or a polymer of at least one water-soluble monomer selected from the group consisting of vinyl acid amides and vinyl heterocyclic compounds.

7. The analytical element of claim 1, wherein said polymeric particulate units have a size of from about 0.1 to about 200 microns.

8. The analytical element of claim 7, wherein said polymeric particulate units have a size of from about 0.3 to about 100 microns.

9. The analytical element of claim 7, wherein said reagent layer has a voids volume of from about 20 to about 85%.

10. An analytical element, comprising a light-transmissive and liquid-impervious support, at least one reagent layer containing at least one reagent which reacts with a component in a fluid sample and at least one development layer provided at a position on said at least one reagent layer on the opposite side to that of said support for permitting the component in said fluid sample to permeate into said at least one reagent layer, wherein at least one reagent layer of said at least one reagent layers is composed of polymeric particulate units having a size of from 0.1 to 200 microns, said polymeric particulate units having a core-shell multilayer structure comprising a hydrophobic core having a degree of swelling of less than 20% which is substantially non-swellable when in contact with a fluid sample, and a hydrophilic outer shell, said core-shell being in an amount of about 25 to about 0.5% by weight and said outer shell being in an amount of about 99.5 to about 75% by weight based on the weight of said polymeric particulate units, wherein the polymeric particulate units are bound to adjacent polymeric particulate units by mutual adhesion of the respective hydrophilic outer shells, said polymeric particulate units forming voids which substantially impede the development of a fluid sample in the lateral direction.

11. The analytical element of claim 10, wherein said polymeric particulate units have a size of from about 0.3 to about 100 microns.

12. The analytical element of claim 10, wherein said reagent layer has a voids volume of from about 20 to about 85%.

13. The analytical element of claim 10, wherein said core consists of a polymer of at least one monomer selected from the group consisting of styrenes, acrylates, methacrylates, acrylonitriles, methacrylonitriles, vinyl halides, vinylene halides, conjugated dienes, crosslinking monomers, and monomers having non-radical polymerizable functional groups.

14. The analytical element of claim 10, wherein said outer shell consists of at least one water-soluble polymer, selected from the group consisting of gelatins, water-soluble celluloses, pullulanes, and water-soluble vinyl polymers, or a polymer of at least one water-soluble monomer selected from the group consisting of vinyl acid amides and vinyl heterocyclic compounds.

15. A method of detecting the presence of a component in a biological fluid suspected of containing said component, said method comprising:
   contacting said fluid with an analytical element comprising a light-transmissive and liquid-impervious support, at least one reagent layer containing at least one reagent which reacts with said component in said fluid and at least one development layer provided at a position on said at least one reagent layer on the opposite side to that of said support for permitting said component in said fluid to permeate into said at least one reagent layer, wherein at least one reagent layer of said at least one reagent layer is composed of polymeric particulate units, each having a core-shell multi-layer structure comprising a hydrophobic core which is substantially non-swellable when in contact with said fluid, and a hydrophilic outer shell, wherein the polymeric particulate units are bound to adjacent polymeric particulate units by mutual adhesion of the respective hydrophilic outer shells, said polymeric particulate units forming voids which substantially impede the development of a fluid sample in the lateral direction; and determining the effect of said component on said reagent in said at least one reagent layer.

16. The method of claim 15 wherein the step of determining the effect of said component on said reagent comprises determining the change in the absorption or emission of electromagnetic radiation of said reagent.

* * * * *